US00PP07874P

United States Patent [19]

Fruehwirth

[11] Patent Number: Plant 7,874

[45] Date of Patent: May 26, 1992

[54] POINSETTIA PLANT '140'

[75] Inventor: Franz Fruehwirth, Encinitas, Calif.

[73] Assignee: Paul Ecke Ranch, Inc., Encinitas, Calif.

[21] Appl. No.: 528,231

[22] Filed: May 24, 1990

[51] Int. Cl.[5] ..... A01H 5/00

[52] U.S. Cl. ..... Plt./86

[58] Field of Search ..... Plt./86, 86.4

[56] References Cited

U.S. PATENT DOCUMENTS 4,724,276 2/1988 Ecke, Jr. ..... 47/58

*Primary Examiner*—Howard J. Locker

*Attorney, Agent, or Firm*—Arnold, White & Durkee

[57] ABSTRACT

Poinsettia '140' is a stiff-stemmed, early flowering cultivar with dark red flower bracts. It has dark green foliage and a strong branching habit. The stem length is relatively short and chemical growth retardants may not be needed to control the height of flowering plants. Because of its early flowering '140' can be grown in a relatively cool greenhouse, making it more economical to grow commercially.

1 Drawing Sheet

BACKGROUND OF THE NEW PLANT

This new Poinsettia cultivar '140' originated as an induced mutation of a seedling from cross pollination in my greenhouse in Encinitas, Calif. The seedling was designated 'I-85'. Cultivar '140' was selected because of its early flowering, short stature, dark red flower bracts and dark green foliage; traits which distinguish it from other Poinsettia cultivars and seem to make it a desirable plant for commercial greenhouse production. Cultivar '140' was strongly self-branching, unlike the parent 'I-85'. Further, '140' is typically shorter than other poinsettia cultivars by several centimeters, including 'I-85'. Because of its stronger branching, '140' typically finishes at an overall height of 35 cm while 'I-85' is nearer 38–40 cm. Cultivar '460', which has some characteristics similar to '140', is significantly taller, attaining a height of about 43 cm after self-branching. After selection, stem cuttings of cultivar '140' were vegetatively reproduced for test purposes in Encinitas, Calif., and clones of this plant were subjected to successive generations of vegetative propagation which demonstrated that its distinctive characteristics hold true from generation to generation.

DESCRIPTION OF THE PHOTOGRAPHS

Poinsettia '140' is illustrated in the accompanying color photographs. The upper photo is a side view of a typical branched plant in full flower. The lower photo is a top view of the same plant showing flower and bract formation.

DESCRIPTION OF THE PLANT

The following is a detailed description of this new Poinsettia as observed in my greenhouse in Encinitas, Calif., during December 1989. Observations were recorded from flowering plants, grown as 3 unpinched plants per pot. The pot was 14 cm. in diameter and 11 cm. in height. Color designations are compared to the 1986 edition of R.H.S. Colour Chart, first published in 1966 by the Royal Horticultural Society, London, England.

The Plant

Origin: Induced mutation 'I-85' (non patented); Cultivar '140' was induced by application of the procedures set forth in U.S. Pat. No. 4,724,276 to 'I-85'.

Classification:

*Botanic.*—*Euphorbia pulcherrima* Willd.

*Common name.*—Poinsettia.

*Cultivar name.*—'140'.

Form: Shrub.

Height: Short.

Growth habit: As a single stemmed plant, upright and short. The application of a chemical growth retardant may not be needed to restrict height for commercial pot plant production. I observed 3 plants in a pot with an overall height of 35 cm. and an overall width of 48 cm. In contrast, 'I-85' attains an overall height of 38–40 cm. The self-branching cultivar, '490', typically attains a height of 43 cm. The bract diameter of individual flowers was 30 cm.

Branching: Poinsettia '140' has self-branching traits. Axillary branches will develop and terminate in a flower without pinching. It may be desirable to pinch '140' and remove all terminal dominance. Then 5–7 axillary branches will develop uniformly. Even after pinching, 'I-85' usually develops 4–5 axillary branches.

Growth rate: Rooting of stem cuttings occurs in 12–18 days under intermittent mist. The plant will flower in about eight weeks under continuous long night conditions and night temperatures of about 16–18 degrees C.

Foliage: The foliage is clean and uniformly dark green from bottom to top of the plant. The leaves are of medium size, leaf blades typically being about 14–15 cm. long and about 9–10 cm. wide with leaf petioles about 6 cm. long.

*Leaf shape.*—Typical leaves are ovate with obtuse bases and acuminate tips. Leaf margins are usually lobed with 1 or 2 indentations of each side of the leaf blade.

*Color.*—Upper side — Dark green, darker than R.H.S. 147A. Under side — Greyed green, darker than R.H.S. 191A.

*Retention.*—The foliage lasts extremely well even under low light intensities in the consumer's home.

Bracts: Generally there are 24–27 uniformly colored bracts of various sizes subtending the cyathia. The primary bracts have blades typically 16–17 cm. long and 10–11 cm. wide with petioles about 3 cm. long.

*Shape.*—Bracts are mostly ovate with obtuse to acute bases and acuminate tips. Primary bracts are lobed with 1 or 2 indentations on either side of the bract. Secondary bracts have entire margins.

*Color.*—Upper side — Dark red, a little lighter than R.H.S. 46A. Under side — Dark red, lighter than R.H.S. 46A.

Flowers: Generally, 15–18 cyathia (flowers) are present when the plant is in full bloom. Each cyathium is about 7–8 mm long and about 5 mm wide, green in color and fringed with red at the distal end. One yellow nectar cup protrudes from the side of each cyathium. The flower pedicel is also green and about 5 mm in length. The stamens protruding from the cyathia are red.

What is claimed is:

1. A new and distinct Poinsettia cultivar, substantially as herein shown and described, characterized by its early flowering, short stature, dark red flower bracts and strong branching habit.

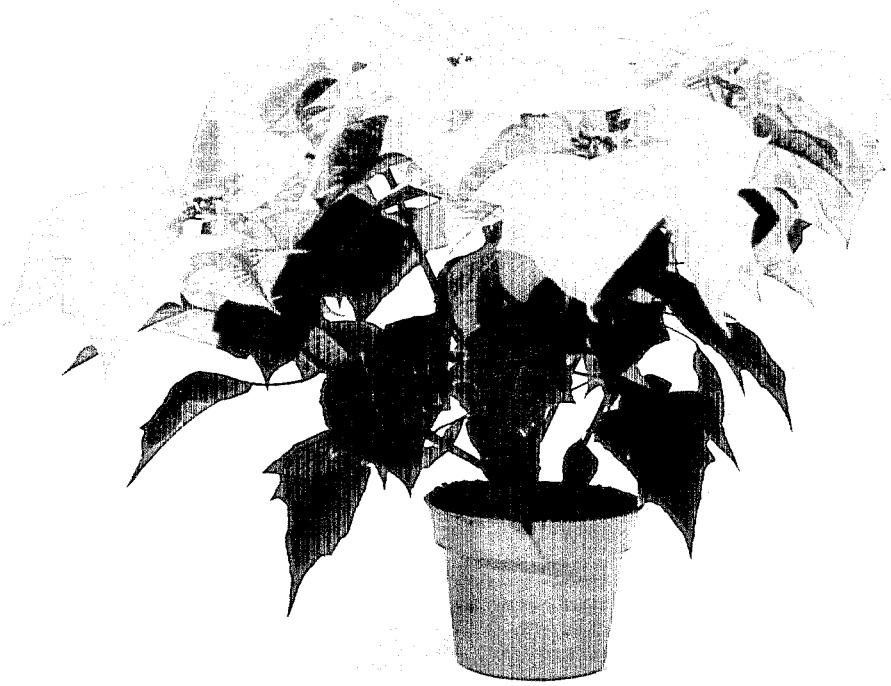
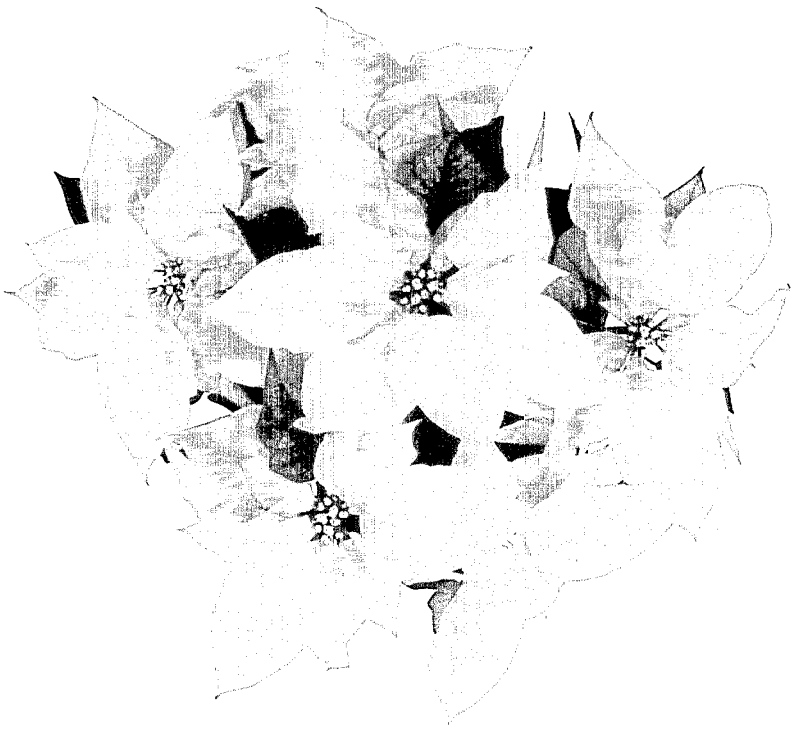

* * * * *